United States Patent

Dietz et al.

[11] Patent Number: 5,879,526
[45] Date of Patent: Mar. 9, 1999

[54] ELECTROCHEMICAL MEASURING SENSOR FOR DETERMINING NITROGEN OXIDES IN GAS MIXTURES

[75] Inventors: Hermann Dietz; Werner Gruenwald, both of Gerlingen, Germany

[73] Assignee: Robert Bosch GmbH, Stuttgart, Germany

[21] Appl. No.: 822,510

[22] Filed: Mar. 24, 1997

Related U.S. Application Data

[63] Continuation-in-part of Ser. No. 669,352, filed as PCT/DE95/01407, Oct. 13, 1995, published as WO96/14575, May 17, 1996, abandoned.

[30] Foreign Application Priority Data

Nov. 8, 1994 [DE] Germany .......................... 44 39 901.4

[51] Int. Cl.[6] .................................................. G01N 27/41
[52] U.S. Cl. .......................... 204/425; 204/412; 204/426; 205/781
[58] Field of Search .................................. 204/421–429, 204/415, 412; 205/781

[56] References Cited

U.S. PATENT DOCUMENTS

| | | | |
|---|---|---|---|
| 3,923,624 | 12/1975 | Beekmans et al. | 204/427 |
| 4,141,800 | 2/1979 | Breuer et al. | 205/781 |
| 4,502,939 | 3/1985 | Holfelder et al. | 204/429 |
| 4,769,124 | 9/1988 | Okada et al. | 204/426 |
| 4,839,018 | 6/1989 | Yamada et al. | 204/426 |
| 4,927,517 | 5/1990 | Mizutani et al. | 204/425 |
| 5,034,112 | 7/1991 | Murase et al. | 204/425 |
| 5,049,254 | 9/1991 | Logothetis et al. | 204/425 |
| 5,071,526 | 12/1991 | Pletcher et al. | 205/781 |
| 5,098,549 | 3/1992 | Friese et al. | |
| 5,273,628 | 12/1993 | Liu et al. | 204/296 |
| 5,304,294 | 4/1994 | Wang et al. | 204/426 |
| 5,397,442 | 3/1995 | Wachsman | 205/781 |

FOREIGN PATENT DOCUMENTS

| | | |
|---|---|---|
| 0257842 | 3/1988 | European Pat. Off. . |
| 3728618 | 3/1988 | Germany . |
| 3908393 | 1/1991 | Germany . |
| 2287543 | 9/1995 | United Kingdom . |

OTHER PUBLICATIONS

Keizer, K., et al., "Progress in Inorganic Membranes", Chemtech, vol. 26, No. 1, pp. 37–41 (Jan. 1996).

*Primary Examiner*—T. Tung
*Attorney, Agent, or Firm*—Venable

[57] ABSTRACT

An electrochemical measuring sensor for selectively determining nitrogen oxides in a gas mixture including oxygen and nitrogen oxides, includes a solid electrolyte layer; a cover layer; and a diffusion channel which is defined between the solid electrolyte layer and the cover layer, and through which the gas mixture diffuses in a diffusion direction. The solid electrolyte layer has provided on a surface thereof a first cathode and a second cathode disposed one after the other in the diffusion direction of the gas mixture within the diffusion channel and exposed to the gas mixture in the order recited, and has provided on an opposite surface thereof at least one anode. The diffusion channel forms a diffusion barrier for the second cathode. The first and second cathodes and the at least one anode are gas permeable and consist of one of a precious metal or a precious metal alloy. The first cathode is provided with a coating which completely covers same, which is impermeable to nitrogen oxides ($NO_x$), and which is permeable to oxygen. The first cathode, a portion of the solid electrolyte, and the at least one anode form a first pumping cell. The second cathode, another portion of the solid electrolyte, and the at least one anode form a second pumping cell. A measuring signal for determining $NO_x$ is measured between the second cathode of the second pumping cell and the at least one anode of the second pumping cell as a limiting current.

8 Claims, 1 Drawing Sheet

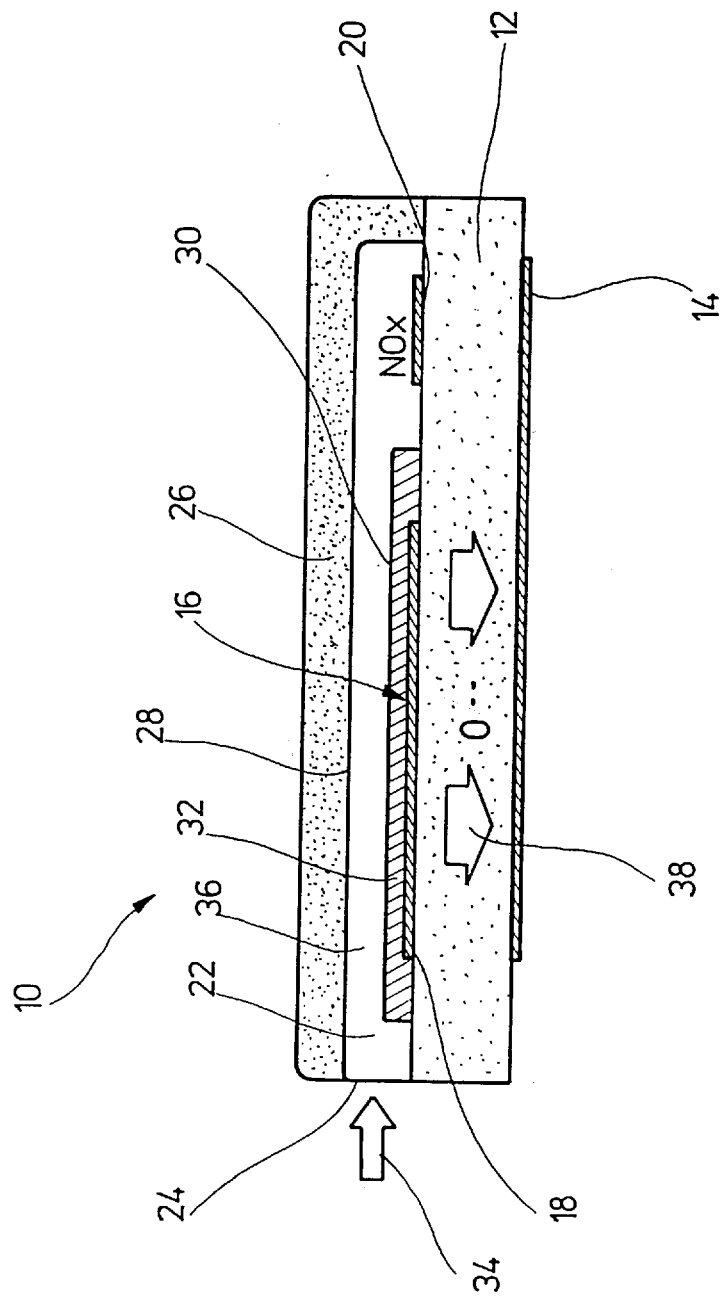

ELECTROCHEMICAL MEASURING SENSOR FOR DETERMINING NITROGEN OXIDES IN GAS MIXTURES

This application is a continuation-in-part of application Ser. No. 08/669,352, filed as PCT/DE95/01407 Oct. 13, 1995 published as WO96/14575 May 17, 1996, now abandoned.

BACKGROUND OF THE INVENTION

1. Field of the Invention

The invention relates to an electrochemical measuring sensor for determining nitrogen oxides in gas mixtures, particularly in exhaust gases of internal combustion engines.

2. Description of the Related Art

It is known that exhaust gases of internal combustion engines, for example diesel engines, contain nitrogen oxides in addition to unburnt fuel components and oxygen. The composition of the exhaust gas is primarily determined by the setting of a fuel-air mixture with which the internal combustion engine is operated. If, for example, fuel is present in a stoichiometric surplus, significant quantities of unburnt or only partially-burnt fuel is present in the exhaust gas, whereas in a stoichiometric surplus of oxygen of the air in the fuel-air mixture, a correspondingly higher concentration of oxygen is noted in the exhaust gas. For setting an optimal fuel-air mixture, it is known to determine the composition of the exhaust gas with a limiting current sensor ($\lambda$ sensor). The limiting current sensor includes a solid electrolyte which is disposed between two electrodes, with one electrode being exposed directly to the exhaust gas and another electrode being exposed to the exhaust gas by way of a diffusion barrier. If a constant voltage is applied to the electrodes, a limiting current is established at the two electrodes due to a difference in oxygen concentrations; this current is measured with a measuring device and evaluated, for example to set the fuel-air mixture with which the internal combustion engine is operated.

A limiting current sensor of this type is known from, for example, DE-PS 37 28 618. In this case, an electrode configured as a pump electrode is disposed in a diffusion channel which is connected on one side to the gas mixture to be measured. Disposed inside the diffusion channel is a diffusion barrier which is designed such that an oxygen partial pressure corresponding to the applied voltage is established at the electrode connected to the exhaust gas by way of the diffusion barrier.

Furthermore, measuring sensors are known in which the one electrode is exposed to the gas mixture to be measured and the other electrode is exposed to a reference gas. Because a difference in oxygen concentrations is established at the electrodes, a voltage is applied to the electrodes which provides a measure for the oxygen concentration in the gas mixture to be measured.

A disadvantage of the known measuring sensors is that they can only be used to determine the oxygen content of the gas mixture to be measured, while other components of the gas mixture are not taken into consideration.

SUMMARY OF THE INVENTION

In contrast, the present invention provides an electrochemical measuring sensor for selectively determining nitrogen oxides in gas mixtures, particularly in exhaust gases of internal combustion engines, the sensor having a limiting current sensor, wherein a cathode of the limiting current sensor exposed to the gas mixture is disposed in a diffusion channel, characterized in that the cathode (16) comprises at least two partial cathodes (18, 20), of which a first partial cathode (18) is provided with a coating (30) which is impermeable to nitrogen oxides ($NO_x$). The electrochemical measuring sensor of the invention, has the advantage that a selective verification of small quantities of nitrogen oxides is also possible in addition to the verification of an oxygen concentration. Because the cathode comprises two partial cathodes, of which a first partial cathode is provided with a coating that is impermeable to the nitrogen oxides, it is advantageously possible to pump the oxygen, to which the coating is permeable, out of the gas mixture so that only the nitrogen oxides still contained in the gas mixture are present at a second partial cathode. These oxides can now be quantitatively and selectively detected as a limiting current signal by the second partial cathode without being influenced by an oxygen concentration. The electrochemical measuring sensor is distinguished by an overall very simple and sturdy design which can be produced with generally-known printing steps, for example in a screen-printing method.

Further advantageous embodiments of the invention ensue from the features disclosed in the dependent claims.

BRIEF DESCRIPTION OF THE DRAWINGS

The invention is described in detail below by way of an embodiment and in conjunction with the associated drawing figure, which shows a schematic, sectional representation through a measuring sensor.

DESCRIPTION OF THE PREFERRED EMBODIMENTS

The figure shows a measuring sensor indicated generally by 10. The measuring sensor 10 includes an essentially wafer-shaped solid electrolyte 12, on whose one side an electrode 14 connected as an anode is disposed. Disposed on the side of the solid electrolyte 12 opposite the anode 14 is an electrode 16 which is connected as a cathode and comprises a first partial cathode 18 and a second partial cathode 20. Both the anode 14 and the partial cathodes 18 and 20 are connected to connections, not shown, of the measuring sensor 10 by way of conductor paths, likewise not shown. The electrodes are porous and gas-permeable, and can be made of platinum, for example. The solid electrolyte 12 is made of, for example, an yttrium-stabilized zirconium oxide. The partial cathodes 18 and 20 are disposed inside a diffusion channel 22. On its one side, the diffusion channel 22 includes an opening 24, and is closed on its other side. The diffusion channel 22 is thus configured as a blind recess. To embody the diffusion channel 22, the measuring sensor 10 has a cover 26, which is disposed as a layer above the solid electrolyte 12 and has a recess 28 which produces the diffusion channel 22. Inside the diffusion channel 22, the first partial cathode 18 is disposed in the vicinity of the opening 24, while the second partial cathode 20 is remote from the opening 24. The first partial cathode 18 is thus disposed between the opening 24 and the second partial cathode 20. The first partial cathode 18 has a coating 30 which completely surrounds the first partial cathode 18 in the direction of the diffusion channel 22. The coating 30 is configured as a selectively oxygen-permeable diaphragm 32, that is, coating 30 is permeable to oxygen gas but is impermeable to $NO_x$ gas. Suitable materials for coating 30 include any coating-forming materials which are impermeable to $NO_x$ gas while being permeable to oxygen gas, such as perovskites. Suitable perovskites include, by way of example but not limitation, $SrCo_{0.8}Fe_{0.2}O_3$; $La_{0.2}Sr_{0.8}CoO_3$; $Y_{0.33}Ba_{0.87}CoO_3$; $La_{0.6}Sr_{0.4}CoO_3(Bi_2O_3)_{0.76}(Er_2O_3)_{0.25}$, and mixtures thereof. Such materials are known in the art and are discussed, for example, in Keizer, K., et al., "Progress in Inorganic membranes", *CHEMTECH*, Vol. 26, No. 1, pages 37–41, January 1996.

The measuring sensor 10 is exposed to a gas mixture, for example an exhaust gas of an internal combustion engine. To this end, the measuring sensor 10 has holding means—not shown in the figure. The gas mixture is present at the anode 14 and, as indicated here by an arrow 34, in the diffusion channel 22. The cover 26 is configured to be impermeable to gas, so that the gas mixture 34 can only enter the diffusion channel 22 by way of the opening 24. The gas mixture 34 typically contains oxygen $O_2$ and nitrogen oxide $NO_x$. Disposed inside the diffusion channel 22 is a diffusion barrier 36 which preferably comprises a porous mixture conductor. In the event of a change in the composition of the gas mixture, the diffusion barrier 36 prevents the composition from being present at the anode 14 and the partial cathodes 18 and 20, respectively, at the same time. Because the partial cathode 18 is disposed in front of the partial cathode 20 inside the diffusion channel 22, the gas mixture 34 only reaches the partial cathode 20 if it has already passed the partial cathode 18. The coating 30 is exclusively permeable to the oxygen $O_2$, so the nitrogen oxides $NO_x$ contained in the gas mixture 34 cannot reach the partial cathode 18.

In the measuring sensor 10 shown in the figure, the illustration of a heating device typically employed by this type of measuring sensor was omitted for the sake of a clear overview. The heating device serves to heat the measuring sensor 10 to a necessary operating temperature of several 100° C.

The measuring sensor 10 shown in the figure functions as follows:

During operation of the measuring sensor 10, a pumping voltage is applied between the partial cathode 18 and the anode 14. A further voltage which is separated from the pumping voltage by circuitry is applied between the partial cathode 20 and the anode 14. The gas mixture 34 diffuses through the diffusion channel 22, passing the coating 30 of the first partial cathode 18. Because the coating 30 is exclusively permeable to the oxygen $O_2$ of the gas mixture 34, the oxygen $O_2$ diffuses toward the partial cathode 18. Because of the pumping voltage applied between the partial cathode 18 and the anode 14, the oxygen $O_2$ is pumped out of the gas mixture 34 inside the diffusion channel 22. The following conversion reaction takes place:

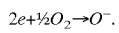

$$2e + \tfrac{1}{2}O_2 \rightarrow O^-.$$

The oxygen $O_2$ is therefore pumped, as oxygen ions $O^-$, from the partial cathode 18 to the anode 14 by the solid electrolyte 12, as indicated by the arrows 38, so that a pumping current flows across the solid electrolyte 12. The pumping current can be measured by a measuring instrument, not shown, for example an ammeter, and forms a reference value for an oxygen concentration present in the gas mixture 34.

The gas mixture 34 present in the diffusion channel 22 now diffuses past the partial cathode 18 to the partial cathode 20. Due to the above-described pumping of the oxygen $O_2$ out of the gas mixture 34, a gas mixture 34 which is essentially free from the oxygen $O_2$ is present at the partial cathode 20. This mixture still contains essentially only the nitrogen oxides $NO_x$. As a consequence of the application of a voltage to the partial cathode 20 and the anode 14, a limiting current signal is formed which is exclusively dependent on the nitrogen oxide concentration in the gas mixture 34. This limiting current signal can be evaluated by a measuring device, for example an ammeter.

Therefore, it is clear that the measuring sensor 10 is suited for detecting, independently of one another, an oxygen concentration, on the one hand, and on the other hand, a nitrogen oxide concentration in a gas mixture. Because the oxygen is pumped out of the gas mixture 34 before the gas mixture reaches the partial cathode 20, the nitrogen oxides $NO_x$ can also be verified quantitatively in small quantities in the gas mixture.

The mode of operation of the measuring sensor 10 can be improved, or adapted to the anticipated gas mixtures 34, by varying the size of the first partial cathode 18 and the coating 30 surrounding it. If the inside surface of the coating 30 or partial cathode 18 is larger, a pumping power of the oxygen-selective pump cell formed by the partial cathode 18 and the anode 14 is improved. Hence, even with large oxygen components in the gas mixture 34, for example if a fuel-air mixture with which the internal combustion engine is operated is in the lean range, the oxygen is reliably pumped out of the gas mixture so that a limiting current signal can be generated for the nitrogen oxide component in the gas mixture 34—even if the proportions are small in comparison to the oxygen. An embodiment in which the diffusion barrier 36 is made of the same material as the coating 30 is preferred here. The diffusion barrier 36 in this instance is provided with pore-forming materials so that it offers a porous structure and is permeable to the nitrogen oxides of the gas mixture and the oxides can diffuse up to the partial cathode 20.

Overall, the measuring sensor 10 can be produced with few printing steps which are known per se and can be controlled, for example in screen printing.

What is claimed is:

1. An electrochemical measuring sensor for selectively determining nitrogen oxides in a gas mixure including oxygen and nitrogen oxides, the electrochemical measuring sensor comprising:

a solid electrolyte layer;

a cover layer; and a diffusion channel which is defined between the solid electrolyte layer and the cover layer, and through which the gas mixture diffuses in a diffusion direction, wherein the solid electrolyte layer has provided on a surface thereof a first cathode and a second cathode disposed one after the other in the diffusion direction of the gas mixture within the diffusion channel and exposed to the gas mixture in the order recited, and has provided on an opposite surface thereof at least one anode, wherein the diffusion channel forms a diffusion barrier for the second cathode, wherein the first and second cathodes and the at least one anode are gas permeable and consist of one of a precious metal or a precious metal alloy, wherein the first cathode is provided with a coating which completely covers same, which is impermeable to nitrogen oxides ($NO_x$), and which is permeable to oxygen, wherein the first cathode, a portion of the solid electrolyte, and the at least one anode form a first pumping cell, wherein the second cathode, another portion of the solid electrolyte, and the at least one anode form a second pumping cell, and wherein a measuring signal for determining $NO_x$ is measured between the second cathode of the second pumping cell and the at least one anode of the second pumping cell as a limiting current.

2. The electrochemical measuring sensor according to claim 1, wherein the diffusion channel has an opening, and wherein the first cathode is disposed within the diffusion channel between the opening of the diffusion channel and the second cathode.

3. The electrochemical measuring sensor according to claim 1, wherein the first pumping cell has a pumping power which can be set by the size of the coating provided on the first cathode.

4. The electrochemical measuring sensor according to claim 1, wherein the diffusion barrier is a structure which permits diffusion.

5. The electrochemical measuring sensor according to claim 4, wherein the the diffusion barrier is comprised of a material which is the same as that of the coating provided on the first cathode.

6. The electrochemical measuring sensor according to claim 5, wherein the diffusion barrier has a porous structure which is permeable to nitrogen oxides.

7. The electrochemical measuring sensor according to claim 1, wherein the coating is comprised of at least one perovskite.

8. The electrochemical measuring sensor according to claim 7, wherein the at least one perovskite is selected from the group consisting of $SrCo_{0.8}Fe_{0.2}O_3$, $La_{0.2}Sr_{0.8}CoO_3$, $Y_{0.33}Ba_{0.87}CoO_3$, $La_{0.6}Sr_{0.4}CoO_3$, and $(Bi_2O_3)_{0.76}(Er_2O_3)_{0.25}$.

* * * * *